United States Patent [19]

Webb

[11] Patent Number: 5,507,417

[45] Date of Patent: Apr. 16, 1996

[54] DEVICE FOR STORING AND DISPENSING STERILE LIQUIDS

[76] Inventor: Garth T. Webb, R.R. #3, 18040 - 20th Ave., White Rock, British Columbia, Canada, V4P 1M6

[21] Appl. No.: 336,272

[22] Filed: Nov. 8, 1994

Related U.S. Application Data

[62] Division of Ser. No. 988,930, Mar. 11, 1993, abandoned.

[30] Foreign Application Priority Data

Sep. 11, 1990 [CA] Canada ................................... 2025105

[51] Int. Cl.⁶ ...................................................... B67D 5/58
[52] U.S. Cl. ................. 222/189.11; 222/212; 222/383.1; 222/494; 222/189.06
[58] Field of Search ..................... 222/212, 494, 222/189, 182, 153, 214, 383, 385, 189.6, 189.11, 383.1

[56] References Cited

U.S. PATENT DOCUMENTS

| | | | |
|---|---|---|---|
| 2,715,980 | 8/1955 | Frick | 222/183 |
| 2,755,974 | 7/1956 | Godfrey | 222/494 |
| 3,088,636 | 5/1963 | Spatz | 222/213 |
| 3,149,758 | 9/1964 | Bush et al. | 222/189 |
| 4,155,487 | 5/1979 | Blake | 222/214 X |
| 4,201,817 | 5/1980 | Aleff | 222/214 X |
| 4,260,079 | 4/1981 | Cary et al. | 222/214 X |
| 4,463,880 | 8/1984 | Kramer et al. | 222/189 |
| 4,530,449 | 7/1985 | Nozawa et al. | 222/189.11 |
| 4,533,068 | 8/1985 | Meierhoefer | 222/189 |
| 4,624,413 | 11/1986 | Corsette | 222/383 X |
| 4,872,596 | 10/1989 | Corsette | 222/383 X |
| 4,938,389 | 7/1990 | Rossi et al. | 222/189 |
| 4,938,393 | 7/1990 | Ericson et al. | 222/380 |
| 4,978,036 | 12/1990 | Burd | 222/207 |
| 5,176,510 | 1/1993 | Nilsson | 417/479 |
| 5,190,191 | 3/1993 | Reyman | 222/383 X |
| 5,197,637 | 3/1993 | Naumann | 222/207 |
| 5,271,553 | 12/1993 | Joulia | 222/401.13 |
| 5,341,965 | 8/1994 | Maas et al. | 222/383 X |

FOREIGN PATENT DOCUMENTS

| | | |
|---|---|---|
| 0363172 | 4/1990 | European Pat. Off. . |
| 2422569 | 11/1979 | France . |
| 3146343A1 | 10/1983 | Germany . |
| 3628197A1 | 2/1988 | Germany . |
| 1000248 | 8/1965 | United Kingdom . |
| 2106877 | 4/1983 | United Kingdom . |

*Primary Examiner*—Kevin P. Shaver
*Attorney, Agent, or Firm*—Klarquist Sparkman Campbell Leigh & Whinston

[57] ABSTRACT

The present invention provides a portable device for storing and dispensing sterile saline for use by contact lens wearers and the like. The device comprises a hollow vessel in which non-sterile saline is stored, which has an outlet on which a housing is mounted. The sterilized saline is dispensed through a second outlet in the housing and a passage communicates between the vessel outlet and the housing outlets. A first valve opens and closes the housing outlet. A liquid-sterilizing filter is mounted in the housing across the liquid passage. A pump for increasing and reducing pressure in the interior of the housing chamber causes the saline to be drawn into an intermediate chamber in the housing and then forces it through the liquid-sterilizing filter and out the housing outlet.

4 Claims, 5 Drawing Sheets

5,507,417

DEVICE FOR STORING AND DISPENSING STERILE LIQUIDS

This is a division of application Ser. No. 07/988,930, filed Mar. 11, 1993, now abandoned.

BACKGROUND OF THE INVENTION

The invention relates to the field of devices for sterilizing liquids, and more particularly to devices for storing and sterilizing saline for ophthalmic purposes, and particularly for contact lens applications.

Sterile saline is required by contact lens wearers for use as a rinse solution, for rinsing the lens prior to inserting the lens in the eye, and also for soaking the lens during the cleaning and disinfecting process.

Sterilization of the saline is generally accomplished using heat, ultra-violet light, or filtration. The saline which has been sterilized in bulk is then stored in plastic squeeze bottles with the addition of chemicals to preserve the sterility. Sterilized saline has also been marketed in aerosol cans, which provide sterile storage without the need for chemical agents. This is accomplished due to the positive pressure within the container which keeps contaminants out. However, the expense and environmental problems associated with aerosol containers make this a less desirable alternative.

There is therefore a need for a simple and portable device for storing and dispensing sterile saline.

SUMMARY OF THE INVENTION

The present invention provides a simple, portable device for storing and dispensing sterile saline which comprises a resilient hollow container having a first outlet, a housing removably mounted on said container and having a second outlet and a passage communicating between said first and second outlet, a liquid-sterilizing filter mounted in said housing in said passage, and valve means for alternately opening and closing said second outlet, whereby pressure applied to said container forces a liquid stored in said container through said filter and out said second outlet when said valve is in an open position.

BRIEF DESCRIPTION OF THE DRAWINGS

In drawings which illustrate a preferred embodiment of the invention.

DETAILED DESCRIPTION OF A PREFERRED EMBODIMENT

Figure 1:
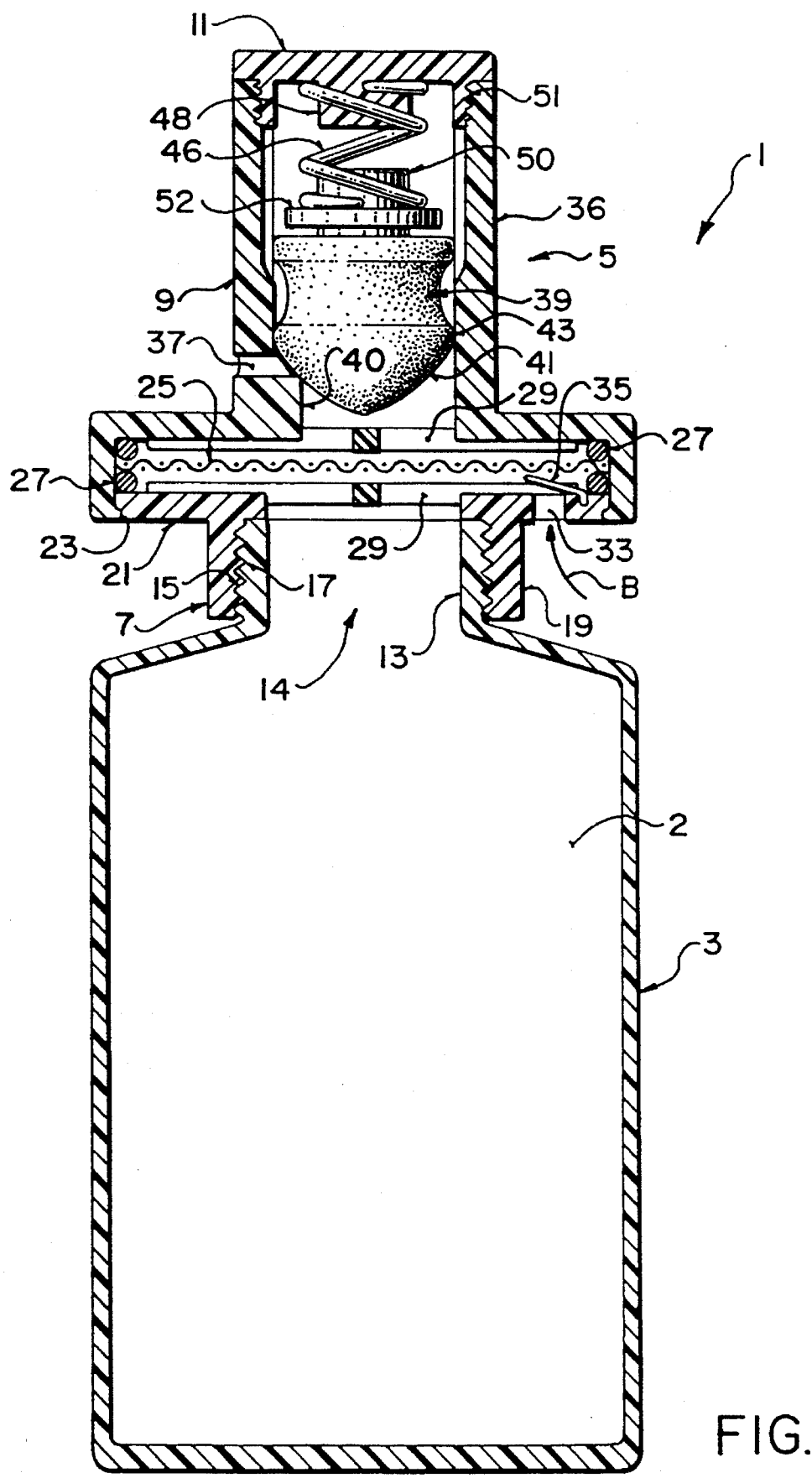
FIG. 1 is a vertical cross-sectional view of the invention with the valve in the closed position.

Referring to FIG. 1, the device of the invention is designated generally as 1. It consists of a resilient squeeze bottle container 3 having hollow interior 2, and a valve and filter housing 5. The squeeze bottle portion 3 is manufactured of a flexible plastic such as a polyethylene or PET, which has sufficient resiliency and memory to return to its original shape after being squeezed. The housing 5 is constructed of a rigid plastic such as a polycarbonate. The housing comprises a base 7, body 9 and cover 11. Container 3 has a circular neck 13 forming open mouth 14 and provided with screw threads 15 on its exterior surface which mate with complementary screw threads 17 on the interior surface of circular extension 19 of base 7. Base 7 has a circular flange 21 which has a snap fit connection with circular lip 23 of body 9.

Mounted in the valve and filter housing 5 between base 7 and body 9 is a circular micro-filter 25. Filter 25 is chosen with a mesh sufficiently fine to be useful for the sterilizing function of the invention. A filter having a 0.2 micron rating is suitable. Such filters are manufactured by Pall Ultrafine Filtration Corporation under the trade-mark ULTIPOR. The filter 25 is sealed in place between base 7 and body 9 by two rubber O-rings 27. To provide rigidity to the filter 25, it is also supported by two plastic inserts 29 located above and below the filter body and having radial arms 30 such that the radius of insert 29 is slightly less than that of filter 25. Inserts 29 could also form part of base 7 and body 9.

Figure 2:
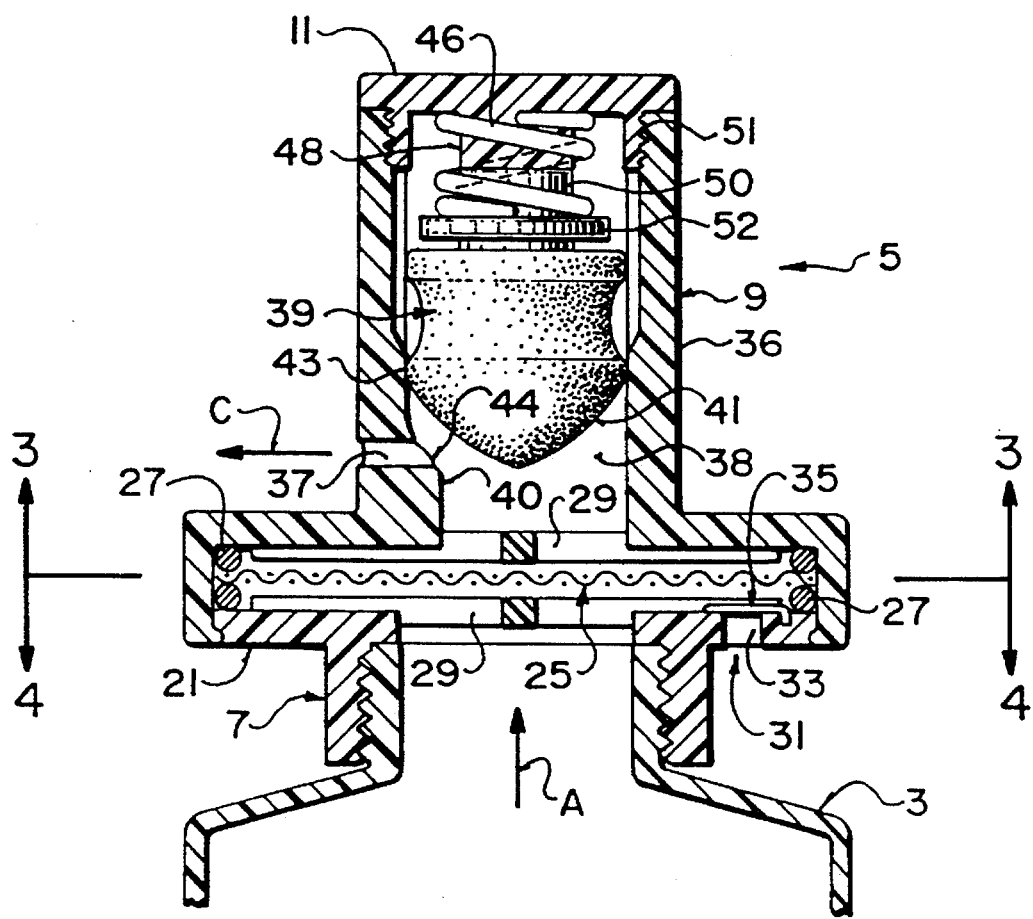
FIG. 2 is a detail of the view of invention shown in FIG. 1, but with the valve in the open position.
Figure 3:
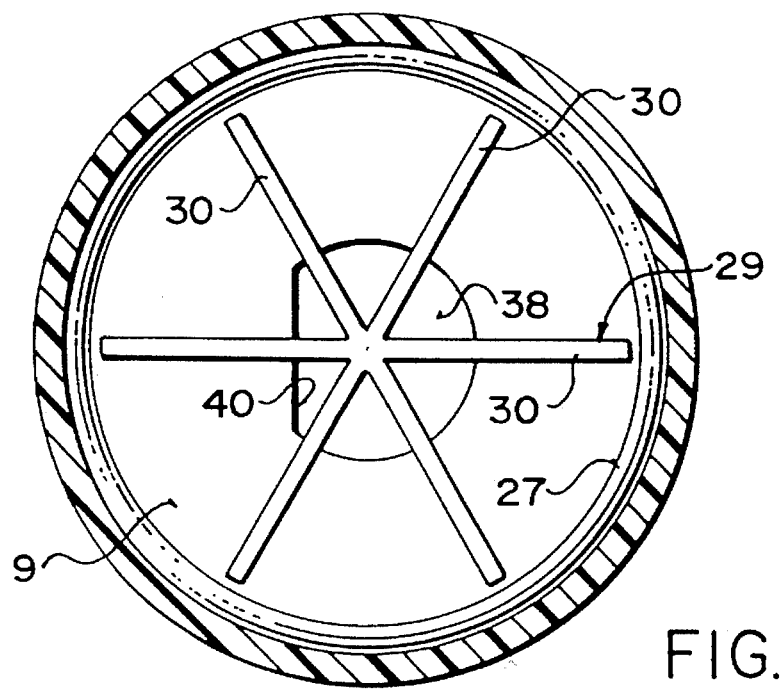
FIG. 3 is a horizontal cross-sectional view of the invention taken along lines 3—3 of FIG. 2.
Figure 4:
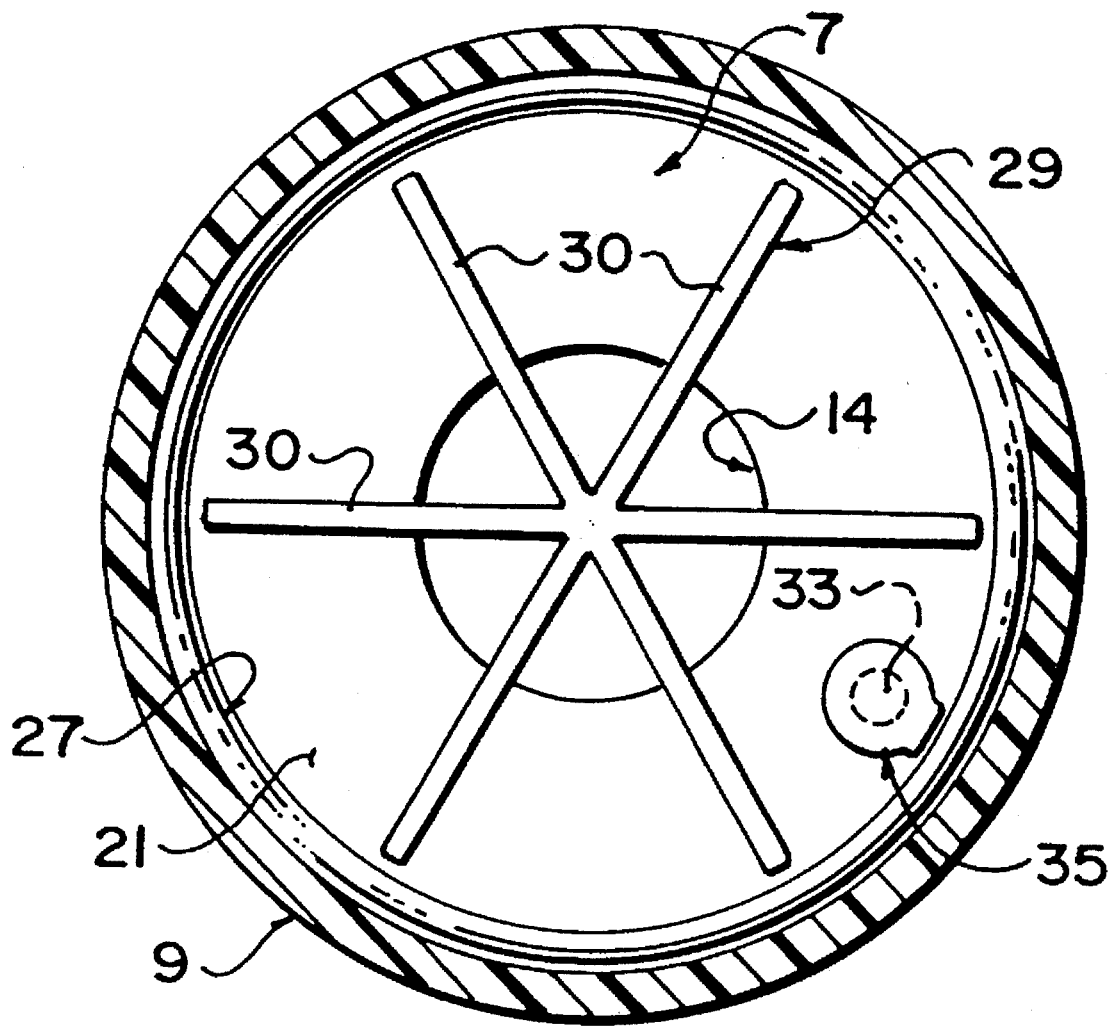
FIG. 4 is a horizontal cross-sectional view of the invention taken along lines 4—4 of FIG. 2.

A valve 31 is provided in base 7 to permit air to enter container 3 after liquid is expelled. It consists of a small opening 33 and a pivoting, inwardly opening flap 35 on the interior surface of flange 21, shown in an open position in FIG. 1 and a closed position in FIG. 2. When the container 3 is squeezed to expel liquid, flap 35 closes opening 33, and when pressure on container 3 is released, flap 35 opens to allow air to enter container 3 in the direction of arrow B, and to allow container 3 to return to its original volume. The same function could be achieved by a plurality of smaller openings. Alternatively, an accordion type of container could replace a squeeze bottle for container 3 which would obviate the necessity for valve 31.

Housing 9 has a hollow cylindrical portion 36 which forms a lower opening 38 and is provided with outlet port 37. Opening 38 is circular but for shoulder 40 which extends into opening 38. Port 37 is alternately opened or closed by rubber valve 39. Valve 39 has a sloping, rounded lower face 41 which ends in a circular lip 43 which seals against the interior surface of cylinder 36. Shoulder 40 has a sloping upper surface 44 which conforms to face 41 to seal port 37 when the valve 39 is in the lower position.

Valve 39 is biassed to its lower, closed position by spring 46, one end of which is held on cylindrical base 48 attached to cover 11, and the other end of which is held on a cylindrical extension 50 of base 52 of valve 39. Cover 11 is screwed into housing 9 by screw threads 51. This permits cover 11 to be removed leaving valve 39 in place. Alternatively, cover 11 can be permanently fixed by an adhesive.

In operation, the hollow interior 2 of container 3 is filled with non-sterile saline and valve and filter housing 9 is then screwed into place. In a rest position, valve 39 closes port 37 due to the action of spring 46. When the user squeezes container 3, flap 35 closes and saline is forced through filter 25 in the direction of arrow A, thereby sterilizing it. Valve 39 moves upwardly opening port 37 and the sterile saline is dispensed from port 37 in the direction of arrow C. When pressure on container 3 is released, valve 39 returns to its closed position, closing port 37, and flap 35 opens to permit air to enter to return container 3 to its original shape.

Figure 5:
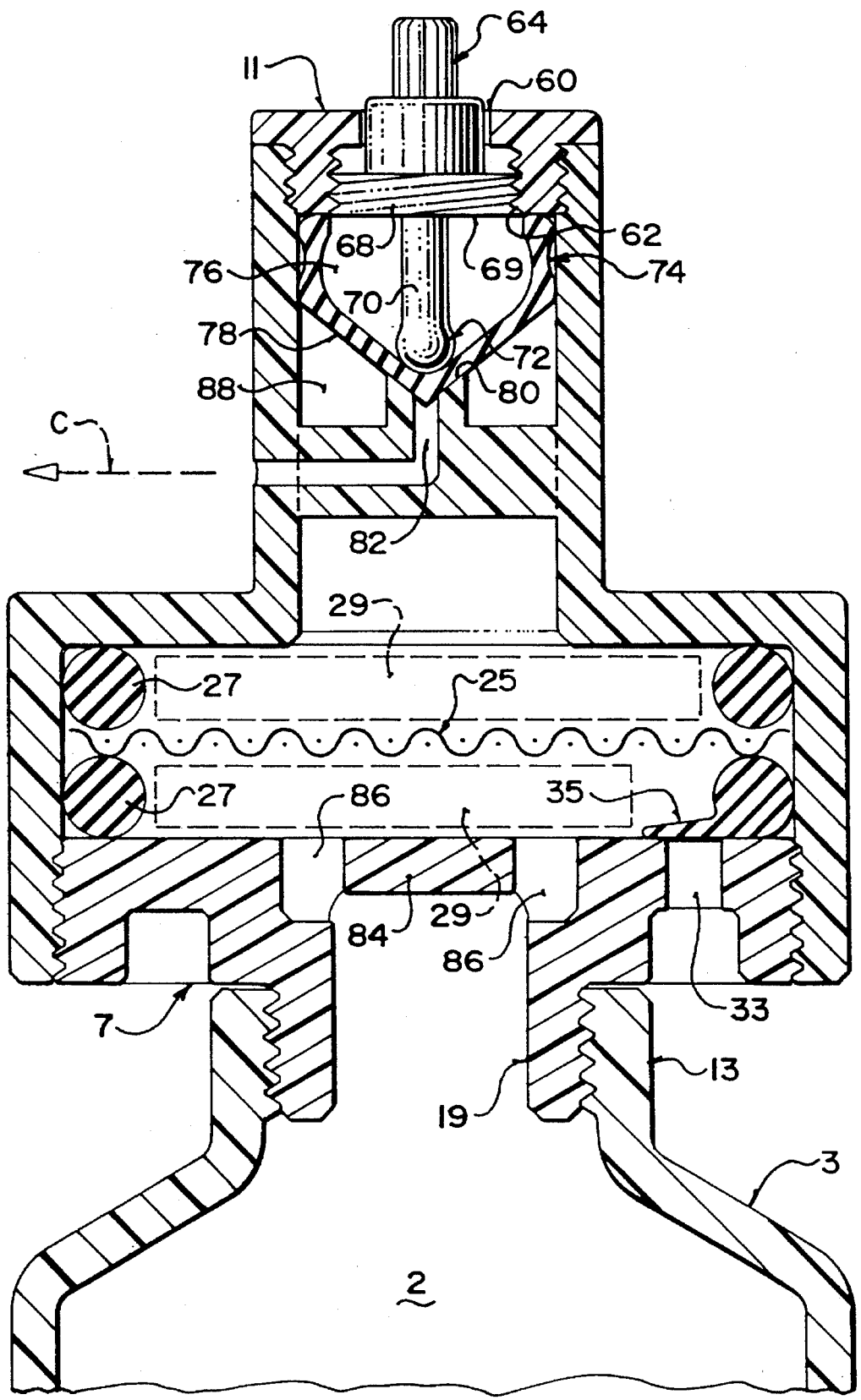
FIG. 5 is a detail of a second embodiment of the invention in vertical cross-section.

A second embodiment shown in FIG. 5 permits valve 74 to be locked in a closed position for transport. In this embodiment cover 11 in turn is provided with opening 60 provided with screw threads 62 into which a knob 64 is screwed by screw threads 66 on disk 68. Attached to the lower surface 69 of disk 68 is a rod 70 with bulbous lower end 72. Rubber valve 74 has a hollow interior 76 into which rod 70 extends, and a flat lower face 78 which seats against shoulder 80 of outlet port 82. Valve 74 is sufficiently resilient in this embodiment, due to the flexing action of its walls, to open and close outlet port 82 in response to the squeezing of container 3 when rod 70 is withdrawn. However valve 74 is locked against opening when rod 70 is screwed tightly against the lower interior surface of valve 74 by rotation of knob 64. In this embodiment, valve 74 could be replaced by a rubber diaphragm stretched across the interior chamber 88 of body 9, and adapted to seal against outlet 82 when pressure is released and open outlet 82 when pressure is applied. In this variation, shoulder 80 would be generally perpendicular to the walls of chamber 88. Also, to improve the flexibility of valve 74, holes could be provided in disk 68 to permit air to flow between the interior 76 of the valve and the atmosphere.

FIG. 5 also shows a second embodiment of base 7 in which the cylindrical flange 19 of base 7 screws into the interior surface of neck 13 of container 3, and a centrally located shield 84 attached to base 7 guards the filter against damage when the container 3 is removed from housing 9. Passageways 86 permit passage of the liquid around shield 84.

Figure 6:
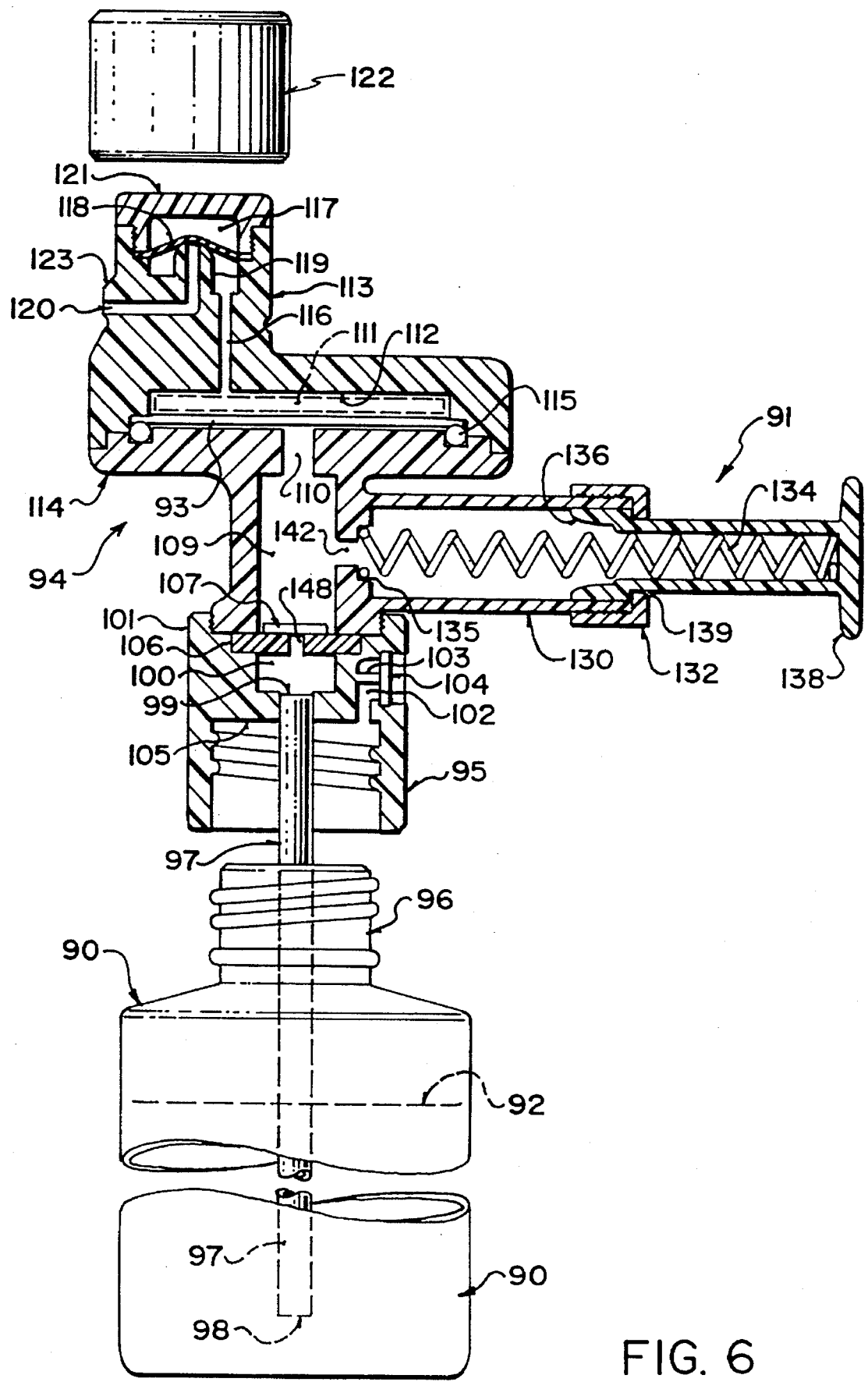
FIG. 6 is a third embodiment of the invention with the filter housing partially removed from the storage container and shown in vertical cross-section.

FIG. 6 illustrates a third embodiment of the invention. In this embodiment, the hollow storage container 90 need not be squeezable, as a plunger 91 is used to provide pressure to the liquid saline 92 to force it through a sterilizing filter 93. The filter housing 94, again constructed of a rigid polycarbonate plastic, has an internally threaded neck 95 which screws onto externally threaded neck 96 of container 90. A hollow feed tube 97 having a lower open end 98 is secured in end piece 105 of housing 94 and extends into container 90 so that end 98 is adjacent the bottom of container 90 when neck 95 is screwed down completely onto neck 96. Tube 97 has an upper open end 99 which opens into a cylindrical chamber 100 formed in end piece 105. Cylindrical wall 101 extends upwardly from neck 95 and has an aperture 102 which communicates with the interior of chamber 90. A support 103 supports filter 104. Passage 102 is covered by a hydrophobic filter 104 which thus permits air to travel through it, but not water or other liquids. Air passing through filter 104 is sterilized. A flap valve could also function in replacement of filter 104 to permit air to enter chamber 90 from the exterior of the container while preventing liquid from escaping.

A filter support 106 supports hydrophobic filter 107 which is circular in shape and is free to slide upwardly in cylindrical chamber 109. Filter support 106 is a plastic disc with a central opening 148 extending from chamber 100 to chamber 109. Filter 107 has a diameter large enough to completely cover opening 148 when the filter is in the lower position. Liquid or air is able to flow through opening 148 and around filter 107 into chamber 109 when filter 107 is raised up off support 106. Filter 107 functions therefore much like flap valve 35 in FIG. 5. Filter 107 could also, for example, be held in a circular frame which guides it against the sides of chamber 109, but permits the flow of liquid between the filter 107 and the walls of chamber 109.

Passageway 110 extends upwardly in housing 94 from chamber 109, with its upper end covered by hydrophillic filter 93. Filter 93 is held in place by O-rings 115. Filter support 111 is a perforated plastic disk which sits in a cylindrical chamber 112 formed between upper housing piece or filter head 113 and lower housing piece 114. O-ring 115 seals the junction of piece 114 and filter 93. In this way liquid flowing up passageway 110 is forced through filter 93 rather than going around its edges. Passage 116 runs from chamber 112 to circular chamber 117 which is covered by a circular rubber membrane or diaphragm 118. Diaphragm 118 is secured at its outer edge by clamp piece 121 and is stretched across central cylindrical extension 119 through the centre of which runs passage 120 to the exterior of the housing. Cap 122 can snap over shoulder 123 to cover the open end of passageway 120.

Plunger 91 consists of a hollow cylinder 130, one end of which is closed by cap 132. Spring 134 sits at one end in a circular groove 135 and the opposite end sits in the hollow cylindrical central channel of plunger 138. Plunger 138 slides through aperture 139, and has attached at one end thereof a flexible plastic piston 136 which slides in cylinder 130. Passageway 142 extends from chamber 144 within cylinder 130 to chamber 109. Spring 134, which biasses the plunger outwardly, is optional. Plunger 138 could be made with a solid shaft. Alternatively, spring-operated plunger 138 could be replaced with an accordion-like plunger which was also biassed outwardly.

In operation, withdrawal of plunger 138 creates a vacuum within chambers 144 and 109. The greater air pressure in container 90 than in chamber 109 therefore causes saline 92 to move up feed tube 97 into chamber 100, through passage 150, around filter 107, filling chamber 109 and 144. Plunger 138 is then pressed inwardly to force filter 107 against support 106, closing aperture 148. Saline from chamber 109 is then forced through filter 93, causing it to be sterilized. Pressure on diaphragm 118 opens passageway 120 permitting the sterilized saline to be dispensed out of passageway 120. Filter 104 permits sterilized air to enter the chamber 90 to replace the ejected saline. Air passing back through filter 107 into the feed tube will also be sterilized. The feed tube 97 is also optional. If it were removed, tilting of the container 90 would be required to place saline in chamber 109.

As will be apparent to those skilled in the art, various modifications and adaptations of the structure above described may be made without departing from the spirit of the invention, the scope of which is to be construed in accordance with the accompanying claims.

I claim:

1. A device for storing and dispensing a sterile liquid comprising a first hollow chamber for receiving said liquid and having a first outlet, a housing mounted on said first outlet having a second outlet and a passage communicating between said first and second outlets, and first valve means for alternately opening and closing said second outlet, characterized by a) a liquid-sterilizing filter mounted in said housing across said passage between said first and second outlets through which filter said liquid passes prior to being forced out said second outlet;

b) an intermediate chamber in said housing between said first and second outlets, second valve means between said first chamber and said intermediate chamber adapted to permit said liquid to flow into said intermediate chamber from said first chamber, and prevent the flow of said liquid from said intermediate chamber into said first chamber when the pressure in said intermediate chamber is increased;

c) pump means for increasing and reducing pressure in the interior of said intermediate chamber, whereby said liquid flows into said intermediate chamber from said first chamber and when pressure is increased in the interior of said intermediate chamber said first valve means is moved to an open position and liquid held in said intermediate chamber is forced through said filter and out said second outlet; and d) an aperture in said housing provided with means adapted to admit air from atmosphere into said first chamber and prevent the exit of liquid.

2. The device of claim 1 wherein said pump means for increasing and reducing pressure in the interior of said chamber comprises a piston movable within a cylinder, said cylinder having an open end communicating with said interior of said intermediate chamber.

3. The device of claim 1 wherein said filter has a mesh having rating of 0.2 microns or less.

4. The device of claim 1 wherein said housing comprises a hollow chamber, and said first valve means is mounted for reciprocal motion in said chamber.

* * * * *